(12) United States Patent
Shen et al.

(10) Patent No.: US 10,513,563 B2
(45) Date of Patent: Dec. 24, 2019

(54) METHOD FOR USES OF PROINSULIN TRANSFERRIN FUSION PROTEINS AS PRODRUGS

(75) Inventors: Wei-Chiang Shen, San Marino, CA (US); Yan Wang, Alhambra, CA (US); Jennica Krankel, Studio City, CA (US)

(73) Assignee: University of Southern California, Los Angeles, CA (US)

( * ) Notice: Subject to any disclaimer, the term of this patent is extended or adjusted under 35 U.S.C. 154(b) by 445 days.

(21) Appl. No.: 13/476,812

(22) Filed: May 21, 2012

(65) Prior Publication Data

US 2013/0130967 A1 May 23, 2013

Related U.S. Application Data

(63) Continuation-in-part of application No. 13/174,520, filed on Jun. 30, 2011, now abandoned.

(60) Provisional application No. 61/361,248, filed on Jul. 2, 2010.

(51) Int. Cl.
| | |
|---|---|
| C07K 19/00 | (2006.01) |
| A61K 38/28 | (2006.01) |
| C07K 14/62 | (2006.01) |
| C07K 14/79 | (2006.01) |
| A61K 47/64 | (2017.01) |

(52) U.S. Cl.
CPC .............. *C07K 19/00* (2013.01); *A61K 38/28* (2013.01); *A61K 47/644* (2017.08); *C07K 14/62* (2013.01); *C07K 14/79* (2013.01); *C07K 2319/00* (2013.01); *C07K 2319/31* (2013.01); *C07K 2319/33* (2013.01); *C07K 2319/74* (2013.01)

(58) Field of Classification Search
None
See application file for complete search history.

(56) References Cited

U.S. PATENT DOCUMENTS 5,672,683 A * 9/1997 Friden et al. ................. 530/350
7,566,565 B2 7/2009 Peters et al.

FOREIGN PATENT DOCUMENTS

| WO | WO 2004/020405 A2 | 3/2004 |
|---|---|---|
| WO | WO 2004019872 A2 * | 3/2004 |
| WO | WO 2007/112005 A2 | 10/2007 |
| WO | 2012003398 A1 | 1/2012 |

OTHER PUBLICATIONS

Rholam (2009, Cellular Molecular Life Science, vol. 66, pp. 2075-2091).*
Yoon (Annals of Biomedical Engineering, 2011, vol. 39, Issue 4, pp. 1235-1251).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Jones et al (Analytical Biochemistry 263, 39-45 (1998)).*
Amet et al (Pharm Res. Mar. 2009; 26(3): 523-528) (Year: 2009).*
Abcam datasheet for recombinant human transferrin protein (Ab155698, downloaded from file:///C:/Users/amccollum/Downloads/datasheet_155698.pdf on Sep. 14, 2018) (Year: 2018).*
Park et al., "Production and characterization of fusion proteins containing transferrin and nerve growth factor" Journal of Drug Targeting, Harwood Academic Publishers GMBH, DE, vol. 6, No. 1, pp. 53-64, Jan. 1, 1998.
Yun et al., "Recombinant granulocyte colony-stimulating factor-transferrin fusion protein as an oral myelopoietic agent" Proceedings of the National Academy of Sciences, vol. 102, No. 20, pp. 7292-7296, May 17, 2005.
Brazil, "Drug delivery: Transferrin' the load" Nature Reviews Drug Discovery, vol. 4, No. 7, pp. 537, Jul. 1, 2005.
Vajo, "Recombinant DNA Technology in the Treatment of Diabetes: Insulin Analogs" Endrocrine Reviews, vol. 22, No. 5, pp. 706-717, Oct. 1, 2001.
Xia, et al,, "Hypoglycemic effect of insulin-transferrin conjugate in streptozotocin-induced diabetic rats" Journal of Pharmacology and Experimental Therapeutics, American Society for Pharmacology and Experimental Therapeutics, vol. 295, No. 2, Jan. 1, 2000.
Widera et al.,, "Mechanisms of TfR-mediated transcytosis and sorting in epithelial cells and applications toward drug delivery" Advanced Drug Delivery Reviews, vol. 55, No. 11, pp. 1439-1466, Nov. 14, 2003.
Shen et al., "Recombinant Transferrin Fusion Proteins for the Activation of Protein Precursors in Liver: The Conversion of Proinsulin to Insulin as a Transferrin Fusion Protein in Hepatoma Cells" Cambridge Healthtech Institute's 10th Annual Peptalk, abstract, Jan. 1, 2011.
Wang, et al., "Inhibition of Glucose Production in Hematoma Cells by Proinsuln-Transferrin Fusion Protein is Facilitated through Transferrin Receptor-Mediated Pathway" AAPS Pharmaceutical Sciences World Congress Abstracts, vol. 12(52), Oct. 1, 2010.

(Continued)

*Primary Examiner* — Brian Gangle
*Assistant Examiner* — Andrea K McCollum
(74) *Attorney, Agent, or Firm* — DLA Piper LLP (US)

(57) ABSTRACT

The present invention provides compositions useful as prodrugs and methods for making the same. The compositions include a fusion protein having a first delivery domain and a second protein precursor domain linked together via a linker sequence. The delivery domain is a protein capable of facilitating entry to a target cells via the endocytotic pathway, such as transferrin. The protein precursor is a prohormone or a profactor, such as proinsulin. Methods of this invention include the steps of selecting a protein suitable as the delivery domain, constructing a vector to encode the fusion protein, and expressing the fusion protein in a suitable expression host. Also disclosed is a method for targeted-delivery of prodrugs to livers and a method of reducing hepatic glucose production.

8 Claims, 9 Drawing Sheets
Specification includes a Sequence Listing.

(56) References Cited

OTHER PUBLICATIONS

Wang et al., "Receptor-mediated activation of a proinsulin-transferrin fusion protein in hepatoma cells" Journal of Controlled Release, pp. 1-7, Jul. 2, 2011.
International search report dated Oct. 21, 2011 for corresponding PCT application PCT/US2011/042708 cites the U.S. patent, forign patent documents and non-patent literature above.
Wang et al., "Proinsilin-transferrin Fusion Protein as a Long-acting and Liver-specific Hypoglycemic Agent" NBC 2012 (2012 AAPS National Biotechnology Conference), p. 1, Feb. 8, 2012 URL: http://abstracts.aaps.org/SecureView/AAPSJournal/d501i2qq1bbhrcb95314.pdf.
International search report dated Sep. 20, 2013 issued in corresponding PCT application PCT/US2013/041867 cites the foreign patent document and non-patent literature listed above.

\* cited by examiner

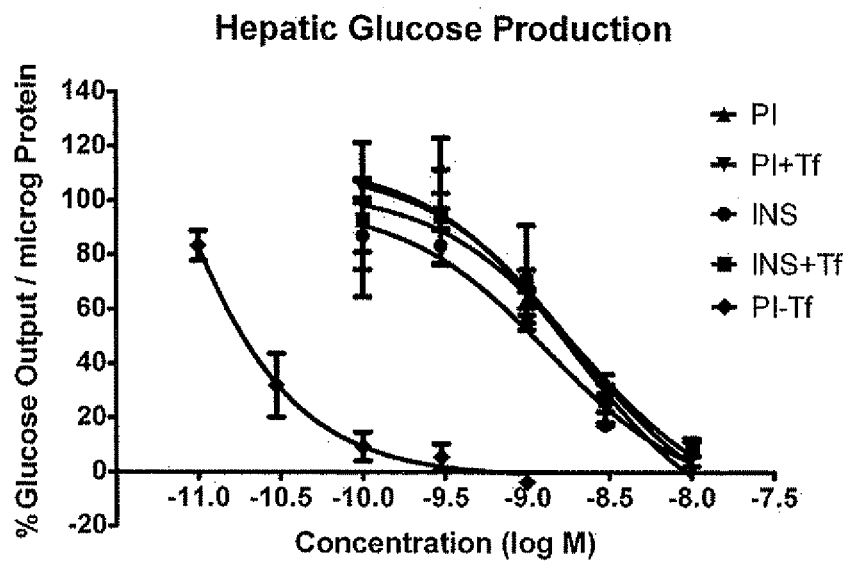
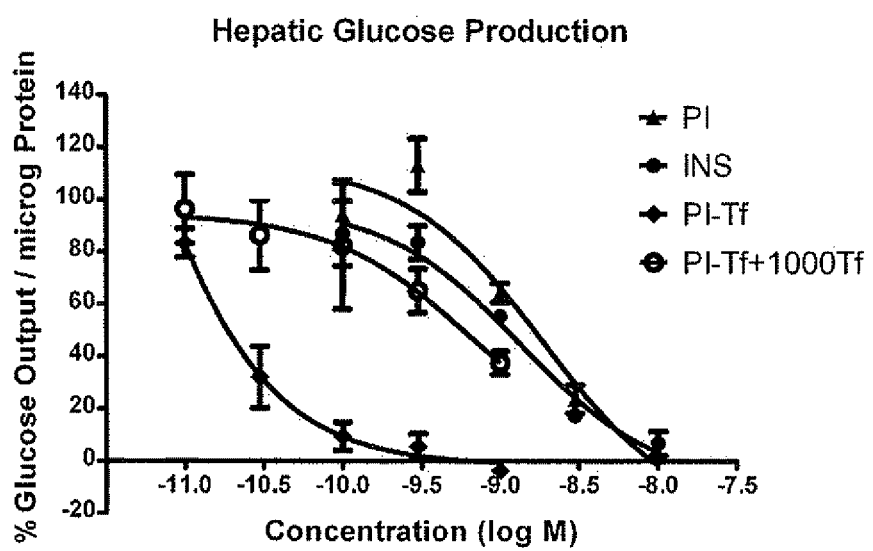
Figure 3 A - B

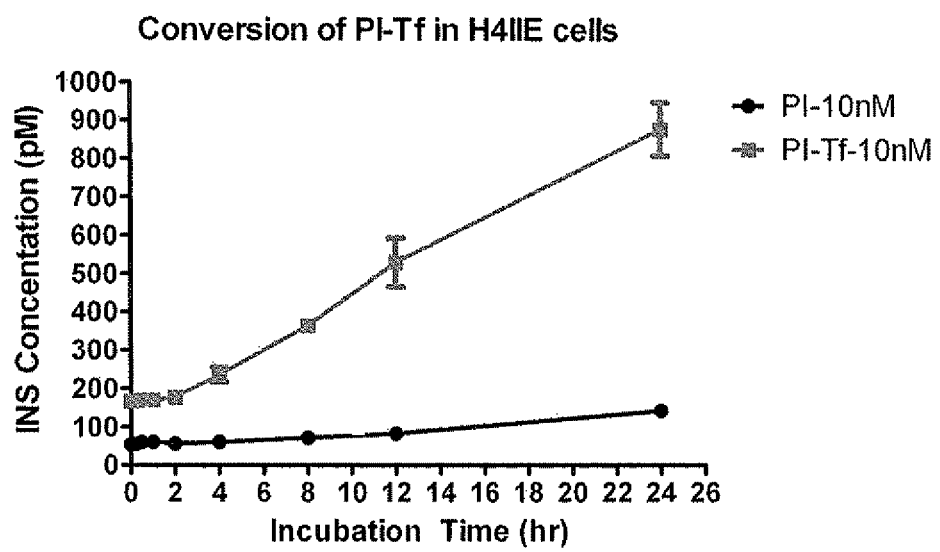
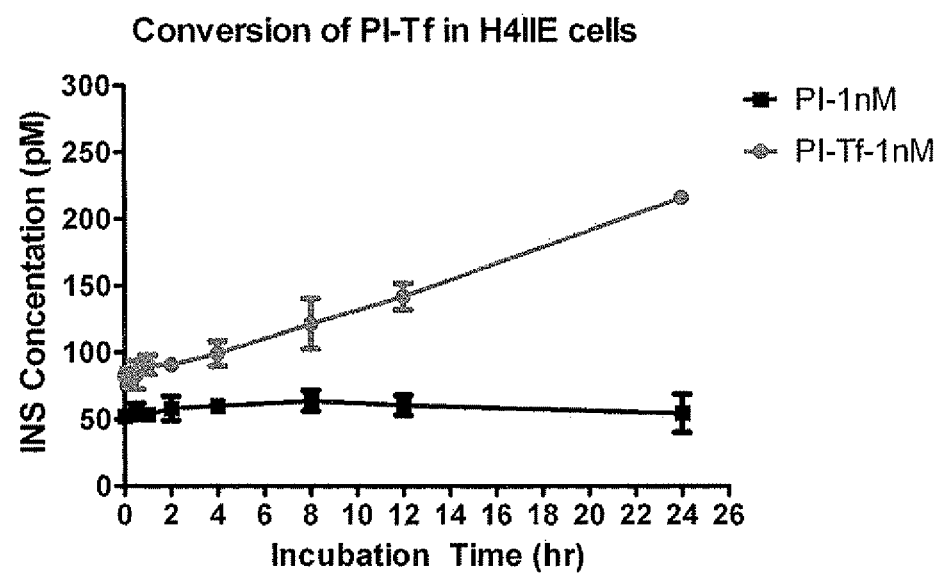
Figure 4

| Injection Groups | ProINS | ProINS-Tf |
|---|---|---|
| $T_{1/2\ a}$ | 0.021±0.001 h | 1.00±0.22 h |
| $T_{1/2\ b}$ | 0.45±0.25 h | 3.08±0.16 h |

US 10,513,563 B2

METHOD FOR USES OF PROINSULIN TRANSFERRIN FUSION PROTEINS AS PRODRUGS

CROSS-REFERENCE TO RELATED APPLICATIONS

This application is a continuation-in-part of U.S. patent application Ser. No. 13/174,520 filed on Jun. 30, 2011, which claims the benefit of U.S. Provisional Application No. 61/361,248 filed on Jul. 2, 2010, the entire contents of which are hereby incorporated herein by reference.

STATEMENT REGARDING FEDERALLY SPONSORED RESEARCH OR DEVELOPMENT

This invention was made with government support under Contract No. GM 063647 awarded by NIH and HIGMS. The government has certain rights in the invention.

FIELD OF THE INVENTION

The invention pertains to the field of drug delivery and protein engineering. More particularly, the invention pertains to methods and compositions for delivering protein-based therapeutics, such as prohormones and profactors, without the need for in vitro chemical or proteolytic processing to produce therapeutically effective drugs.

BACKGROUND OF THE INVENTION

A number of biologically active peptides or proteins, including hormones, cytokines, neuropeptides and growth factors, are initially generated in the form of larger, inactive precursor peptides. These precursor peptides, or propeptides, including prohormones and profactors, generally require specific intracellular proteolytic processing to turn them into their active forms for biological functions [1, 2]. In terms of protein manufacturing, the precursor forms of the peptides are often first synthesized instead of the mature forms. This is because the mature forms of the peptides often have complex conformations, low expression yield, or are structurally unstable. In terms of protein drug delivery, the propeptides, but not the mature peptides, are linked to another protein moiety through chemical conjugation or recombinant fusion to achieve specific delivery goals and enhance overall protein stability [3]. Therefore, in order to exhibit biological activity, the propeptides need to be processed and activated, which is an important and challenging step in the production of recombinant therapeutic proteins.

Conventional methods of delivering the prodrugs generally involve chemical conjugation to link together the propeptide with a delivery protein. However, the major obstacle for chemically conjugating the two domains is that the composition and size of the final product can be heterogeneous, which is unacceptable for therapeutic use. Therefore, there still exists a need for a better approach to form fusion proteins that link together a delivery domain with a prodrug domain.

SUMMARY OF THE INVENTION

The present invention is based on the unexpected discovery that in transferrin receptor-mediated endocytosis, the intracellular compartments of hepatocytes and epithelial cells has the ability to convert proinsulin to insulin. Inspired by this discovery, the inventors have conceived and reduced to practice a method of formulating a protein-based drug by conjugating a propeptide of a protein factor with a tranferrin domain. For example, an insulin-based protein drug may be formed by conjugating the propeptide of insulin (i.e. proinsulin) with transferrin. The proinsulin-transferrin conjugate or fusion protein will be converted to fully active insulin-transferrin when incubated with hepatocytes. In addition to acting as an activation element, the transferrin moiety can further increase the stability and sustained activity of the insulin or other therapeutic peptides compare to their non-conjugated counterparts.

It will be recognized by those skilled in the art that many propeptides of protein factors, such as proinsulin and proglucagon, cannot be used as drugs unless they have been converted to the active peptides by chemical or proteolytic treatment to cleave specific peptide bonds, such as the removal of c-peptide from proinsulin. Alternatively, insulin can be synthesized by two-peptide recombinant method which involves the CNBr treatment to produce A- and B-chain separately followed by the oxidoreductive reaction to form the interchain disulfide bonds [4]. Such modification processes after the production of the propeptides is both technically-challenging and cost-inefficient for therapeutic peptide production. The present invention enables the use of propeptides as drugs without additional chemical or enzymatic processing.

Reduction of hepatic glucose production has been targeted as a strategy for diabetes treatment. Insulin (INS) bioactivity can affect both hepatic glucose production as well as peripheral glucose disposal. Normally, the pancreas delivers INS directly into the hepatic portal vein, and therefore the liver is exposed to high concentrations of INS resulting in a greater effect on hepatic glucose production (HGP). With conventional INS therapy, INS and/or INS analogs are administered subcutaneously, resulting in an under-insulinized liver. The effects in peripheral glucose disposal are subsequently greater, leading to metabolic abnormalities including excessive glycemic fluctuations, dyslipidemia, reduction of plasma IGF-1, and elevated plasma levels of growth hormone [9]. Therefore, an INS therapeutic with greater effect on HGP than peripheral glucose disposal would offer an advantage over the current treatment regiments. It is an unexpected discovery of the present invention that fusion proteins of the present invention are capable of targeted delivery to liver in vivo, in particular, proinsulin-transferrin fusion proteins described herein are capable of targeted delivery to liver in vivo.

Accordingly, in one aspect, the present invention provides a fusion protein useful as a prodrug. Fusion proteins in accordance with embodiments of this aspect of the present invention will generally having a first delivery domain linked to a second protein precursor domain via a linker sequence. The delivery domain is a protein capable of facilitating entry to a target cell via the endocytotic pathway. The second protein precursor domain is preferably a prohormone or a profactor.

In another aspect, the present invention also provides a method for delivering a protein precursor domain to a subject in need of said precursor domain. Methods in accordance with embodiments of this aspect of the present invention will generally include the steps of forming a fusion protein having a delivery domain linked to the protein precursor domain; and administering said fusion protein to the patient.

In yet another aspect, the present invention also provides a method for forming a fusion protein useful as a prodrug. Methods in accordance with embodiments of this aspect of the invention will generally include the steps of selecting a protein useful as a delivery domain for a protein precursor; constructing a vector encoding said delivery domain linked to said protein precursor via a suitable linker sequence; and expression said fusion protein in a suitable expression host.

In still another aspect, the present invention also provides a method for extending a protein precursor domain's half-life in plasma. Methods in accordance with embodiments of this aspect of the invention will generally include the steps of conjugating the protein precursor domain to a transferrin domain prior to introducing the protein precursor domain into the plasma. Here the transferrin domain acts as a half-life extending element to extend the plasma half-life of the protein precursor in the plasma.

In still a further aspect, the present invention also provides a method for extending a therapeutic effect of a protein precursor in a subject. Methods in accordance with embodiments of this aspect of the invention will generally include the steps of conjugating the protein precursor to a transferrin domain so as to form a fusion protein having the protein precursor domain linked to the transferrin domain via a linker sequence. Here the transferrin domain acts as a therapeutic effective stabilizing element that extends the therapeutic effective time of the protein precursor.

In still yet another aspect, the present invention also provides a method for targeting a protein precursor prodrug to a the liver of a subject. Methods in accordance with this aspect of the invention will generally include the steps of administering to the subject a prodrug, wherein the prodrug is a fusion protein comprising a first liver delivery domain linked to a second protein precursor domain via a linker sequence. The liver delivery domain is a protein capable of targeted delivery to liver in vivo and, more preferably, also facilitating entry to liver cells via the endocytotic pathway. Preferably, the liver delivery domain is transferrin. The second protein precursor domain is preferably a prohormone or a profactor. In one preferred embodiment, the fusion protein is a Proinsulin-Transferrin fusion protein.

Other aspects and advantages of the invention will be apparent from the following description and the appended claims.

BRIEF DESCRIPTION OF THE DRAWINGS

FIG. 3 shows graphs of the production of glucose by hepatoma H4IIE cells. They demonstrate the activity of PI-Tf fusion protein in inhibiting hepatic glucose production is higher than that of insulin and proinsulin. Furthermore, FIG. 3B shows that the activity of PI-Tf can be abolished in the presence of a large excess of Tf, suggesting that the activity is mediated by TfR binding. (A) Inhibition curve of proinsulin, insulin and PI-Tf fusion protein. (B) Increased hepatic glucose production was blocked by 1000-fold Tf co-incubation.

FIG. 4 shows graphs for the measurement of insulin in the solutions. They demonstrate the conversion of PI-Tf to insulin-Tf in the presence of hepatoma H4IIE cells.

DETAILED DESCRIPTION

Figure 1:
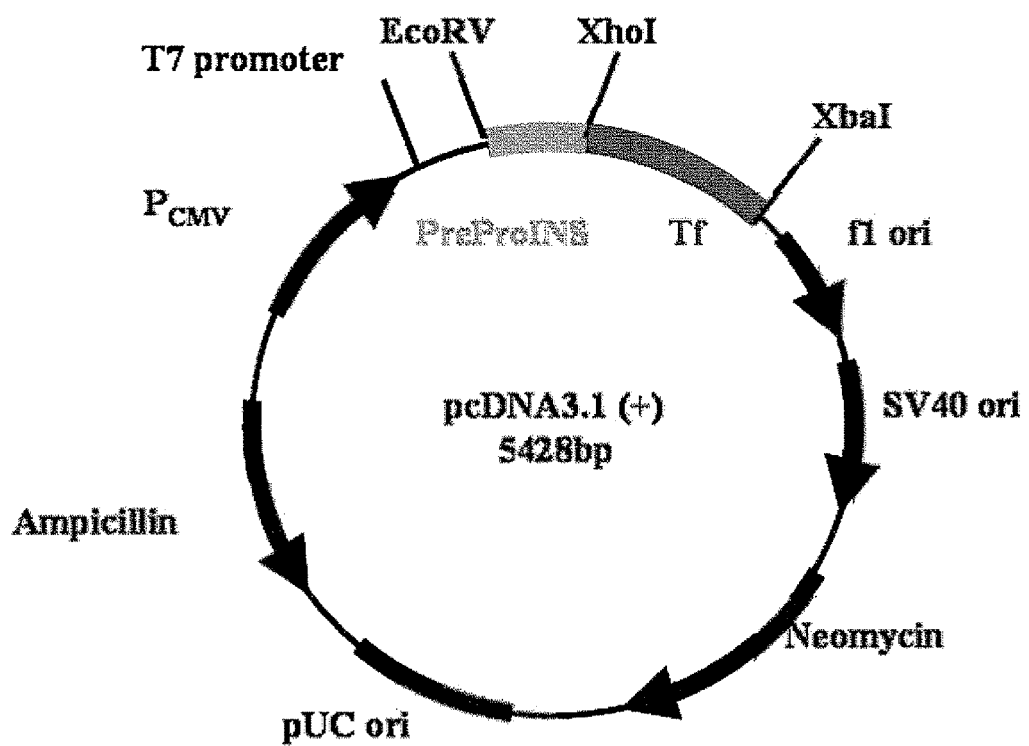
FIG. 1 illustrates the preproinsulin-Tf fusion gene construct in pcDNA 3.1(+) vector.

As used herein, the term "protein precursor" refer to inactive proteins or peptides that can be turned into an active form by posttranslational modification. Exemplary "protein precursor" may include proinsulin, proglucagon and proopiomelanocortin, but are not limited thereto.

As used herein, the term "prodrug" refers to a pharmacological substance that is administered in an inactive or significantly less active form, but becomes activated in vivo through metabolic activities either intracellularly or extracellularly. Exemplary prodrugs may include prohormones and other profactors.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless Unless otherwise indicated, all terms used herein have the meanings given below, and are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel F M et al. (1993) Current Protocols in Molecular Biology, John Wiley & Sons, New York, N.Y., for definitions and terms of the art. It is to be understood that this invention is not limited to the particular methodology, protocols, and reagents described, as these may vary.

The term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

All publications cited herein are expressly incorporated herein by reference for the purpose of describing and disclosing compositions and methodologies that might be used in connection with the invention.

Proteins suitable as the delivery domain will depend on the target cells. Preferably, the protein is one that can facilitate entry to the target cell with the endocytotic pathway.

The linker sequence is preferably short and stable. In some embodiments, the linker is resistant to protyolytic cleavage so that the fusion protein remain intact in vivo. In other embodiments, the linker sequence is designed to be cleaved under suitable environments, such as under acidic or proteolytic conditions of the endocytic vesicle.

As a demonstration, the inventors have obtained a fusion protein of proinsulin-transferrin and have demonstrated that the fusion protein can be converted to insulin-transferrin in liver cell cultures. Unlike the inactive proinsulin, proinsulin-transferrin fusion protein, after incubated with liver cells, possesses higher activity in gluconeogenesis and equal activity in glucose transport when compared to active insulin. Thus, demonstrating that a fusion protein in accordance with embodiments of this invention are useful as prodrugs.

The present invention will now be further illustrated by referring to specific embodiments as shown in the following examples and the accompanying figures. It will be understood that the following examples are provided in order to demonstrate and further illustrate certain embodiments and aspects of the present invention and are not to be construed as limiting the scope thereof. Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims.

EXAMPLES

Example 1

PI-Tf Recombinant Fusion Protein Expression and Characterization

Figure 2:
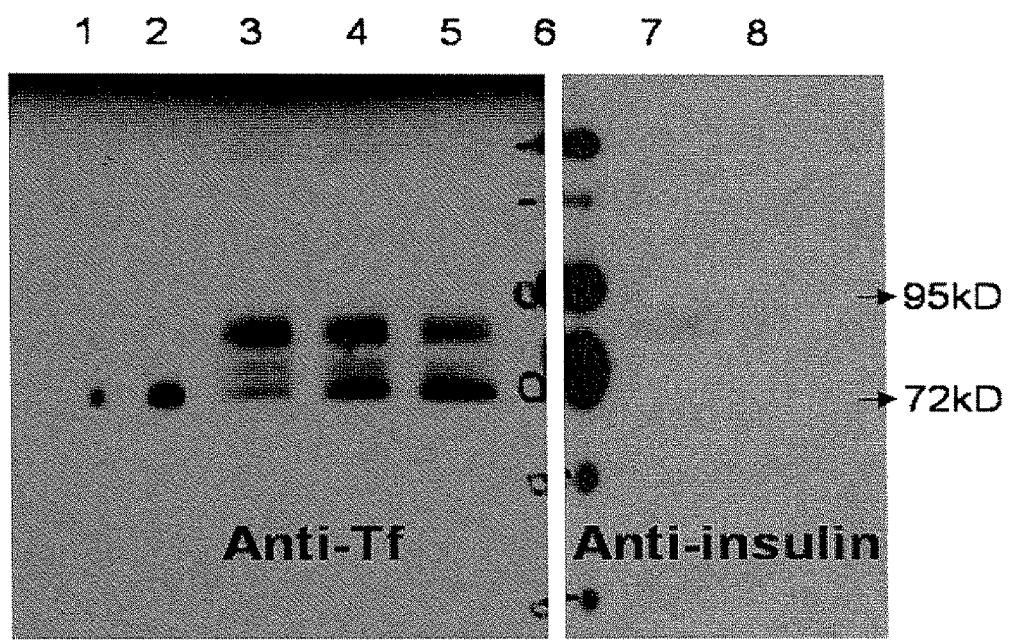
FIG. 2 shows the results of Western blot of PI-Tf fusion protein using anti-Tf and anti-(pro)insulin antibodies, demonstrating the expression of both Tf and proinsulin in the fusion protein. Lane 1 to 5 is anti-Tf blot, and lane 7 is anti-(pro)insulin blot. Lane 1: 5 ng apo-Tf Lane 2: 20 ng apo-Tf. Lane 3: PI-Tf. Lane 4: 5 ng apo-Tf+PI-Tf. Lane 5: 20 ng apo-Tf+PI-Tf. Lane 6: Marker. Lane 7: PI-Tf.

Preproinsulin sequence (NM_000207) (SEQ ID NO: 1) fused in frame with Tf sequence (NM_001063) (SEQ ID NO: 2) was engineered into pcDNA3.1 (+) expression vector (Invitrogen, CA) by molecular cloning methods (FIG. 1). Plasmids containing preproinsulin-Tf fusion gene were transiently transfected to HEK 293 cells through polyethylenimine-mediated DNA transfection. Conditioned serum-free media were collected and concentrated by labscale tangential flow filtration system (Millipore, MA), and then ultra-filtered (CENTRICON®, Millipore, MA). PI-Tf fusion protein was characterized and quantified by Western blot using both anti-Tf (Sigma, MO) and anti-(pro)insulin antibodies (Abcam, MA). Anti-Tf and anti-(pro)insulin Western blots demonstrated the presence of a major band with molecular weight ~89 kD, which indicated that PI-Tf fusion protein was successfully expressed and secreted into media. A leucine-glutamate dipeptide sequence was introduced between proinsulin and Tf due to the XhoI restriction enzyme cutting site. The Tf shown on Lane 3 of FIG. 2 came from the original serum-free cell culture medium, CD 293 (Invitrogen), instead of production from transfected HEK293 cells. The dipeptide linker remained stable during production process.

Example 2

Enhanced Inhibition of Hepatic Glucose Production by PI-Tf Fusion Protein in H4IIE Hepatoma Cells Rat hepatoma H4IIE cells were cultured in high-glucose DMEM containing 10% fetal bovine serum. Upon confluency, cells were treated with different drugs for 24 hrs at 37° C. Cells were washed twice with phosphate buffered saline. Glucose production media consisting of serum-, glucose- and phenol red-free DMEM supplemented with 2 mM sodium pyruvate and 40 mM sodium DL-lactate were added to cells for additional 3-hr incubation. The supernatant was harvested and applied to measure glucose concentrations using the AMPLEX® Red Glucose/Glucose Oxidase kit (Invitrogen, CA) [5]. Cells were lysed in 1 M NaOH, and protein amount was quantified by BCA (Thermo Scientific, IL).

Proinsulin and insulin exhibited comparable inhibitory activities in glucose production with $IC_{50}$ values of 1441.3±1641.6 pM and 1093.9±105.6 pM, respectively (FIG. 3A). Proinsulin bound to insulin receptor, but it had a considerably lower binding affinity than insulin [6]. However, the higher stability of proinsulin allowed itself a slower degradation rate, which may result in similar activity as insulin in the 24 hr-incubation assay. PI-Tf fusion protein, with an $IC_{50}$ value of 4.60±5.78 pM, exerted ~300-fold stronger activity than proinsulin and insulin. However, equimolar mixture of pro insulin/insulin and Tf did not significantly increase the inhibitory activity as fusion protein did. It is consequently suggested that the enhanced inhibition was due to the fusion of the two moieties. Co-incubation of fusion protein with excess Tf (1000-fold) was able to block the increased inhibition, allowing the activity to reduce to that of insulin and proinsulin. However, no blocking effects were observed with excess albumin incubation (FIG. 3B). Therefore, introducing a Tf moiety to proinsulin as one single fusion protein can significantly enhance proinsulin's hepatic glucose inhibitory capacity.

Example 3

Conversion of PI-Tf to Insulin-Tf Fusion Protein by Hepatoma Cells

Rat hepatoma H4IIE cells (ATCC, VA) were treated with PI-Tf fusion protein in DMEM medium and incubated at 37° C. Media were collected at different time points, and subjected to insulin- and proinsulin-specific radioimmunoassays (Millipore, Mass.). Proinsulin and insulin concentrations were obtained based on standard curves from radioimmunoassays. After treatment in H4IIE cells for up to 24 hr, an insulin-containing species was continuously generated from PI-Tf fusion protein-treated samples, but not proinsulin-treated samples (FIG. 4). The generated insulin-containing species was suggested to be insulin-Tf instead of released insulin, since the two moieties were linked through stable peptide bonds. The conversion efficiency of PI-Tf to insulin-Tf was estimated 8.8% when dosed with 10 nM PI-Tf and 21.6% when dosed with 1 nM PI-Tf. These results demonstrated that the prohormone fusion protein PI-Tf can be converted to insulin-Tf in hepatoma cells. It also indicated that this hepatic conversion process was mediated by Tf, presumably occurring inside the intracellular recycling compartments during TfR-mediated endocytosis and recycling.

Example 4

Pretreatment of PI-Tf Fusion Protein in H4IIE Hepatoma Cells Leads to Increased Receptor Binding Affinity and Enhanced Stimulation of Glucose Transport Insulin receptor binding assay was performed using H4IIE hepatoma cells [7]. [125I]-TyrA14 insulin (Perkin Elmer, Mass.) and various concentrations of unlabeled fusion proteins were treated to cells at 4° C. for 2 hr. Cells were washed twice with phosphate-buffered saline, and lysed with 0.1 N NaOH at RT. Radioactivity of total cell lysates was measured by gamma-counter. Protein amount were quantified by BCA assays.

Figure 5:
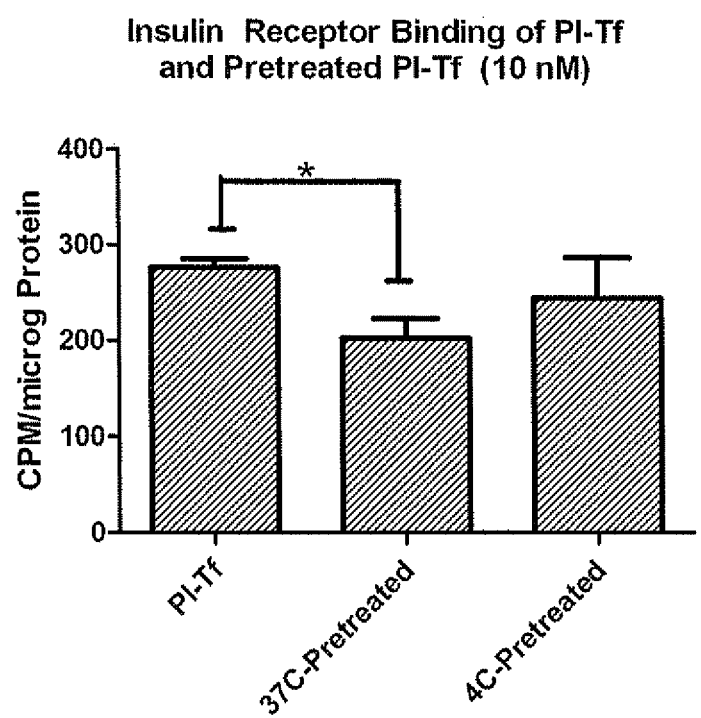
FIG. 5 shows a bar graph illustrating the competition of insulin receptor binding. It demonstrates the improved insulin receptor binding affinity of PI-Tf fusion protein which is preincubated in H4IIE cells under 37° C.

Compared with insulin, proinsulin exhibited a ~100-fold lower binding affinity to insulin receptor on H4IIE hepatoma cells. In order to validate the hepatic conversion of PI-Tf to insulin-Tf, the binding affinity of H4IIE-pretreated PI-Tf fusion protein was measured. Briefly, cells were first treated with PI-Tf at either 37° C. or 4° C. for 1 hr, and subsequently equilibrated at 4° C. for 15 min prior to the addition of [125I]-TyrA14 insulin. Cells were then incubated for 2 hr at 4° C. to allow sufficient binding. Compared with non-treated fusion protein, 37° C.-pretreated PI-Tf fusion protein solutions exhibited a significantly increased binding capacity (FIG. 5). It is suggested that the increased binding might result from insulin-Tf generated during pretreatment in hepatoma cells. Besides, no significant changes were observed for the 4° C.-pretreated PI-Tf. These data indicated that the hepatic conversion to insulin-Tf was not processed by proteases on the cell membrane, whereas it required a cellular internalization to allow intracellular enzymatic processing of PI-Tf fusion protein. The internalization process was suggested to be facilitated through Tf-TfR-mediated endocytosis and recycling.

Insulin is known to promote glucose uptake in muscles and adipose tissues. To test whether PI-Tf and H4IIE-pretreated PI-Tf are active in glucose uptake stimulation, a glucose uptake assay was established using differentiated adipocytes as described previously [8]. Briefly, preadipocytes (murine 3T3-L1 fibroblasts) were induced to differentiate by a hormone cocktail consisting of bovine insulin, dexamethasone and 3-isobutyl-1-methylxanthine. After 10-14 days, cells reached full differentiation. Adipocytes were serum-starved prior to experiments. Cells were incubated with different drugs for 30 min in Krebs-Ringer phosphate (KRP) buffer supplemented with 0.1% bovine serum albumin. Glucose uptake was measured by the addition of 2-deoxy-D-[2, 6-3H] glucose (Perkin Elmer, Mass.). The reaction was stopped after 10 min by aspiration, and cells were washed four times with ice-cold KRP buffer. Cells were lysed with 0.1 M NaOH/0.1% SDS in KRP. Radioactivity was quantified by scintillation counting. Results were normalized for protein amount measured by BCA assays. For PI-Tf pretreatment in H4IIE cells, 10 nM of fusion protein solutions were dosed to H4IIE cells. After 24 hr incubation, the protein solutions were centrifuged, and the supernatants were collected to evaluate their activity of glucose uptake stimulation in adipocytes.

Figure 6:
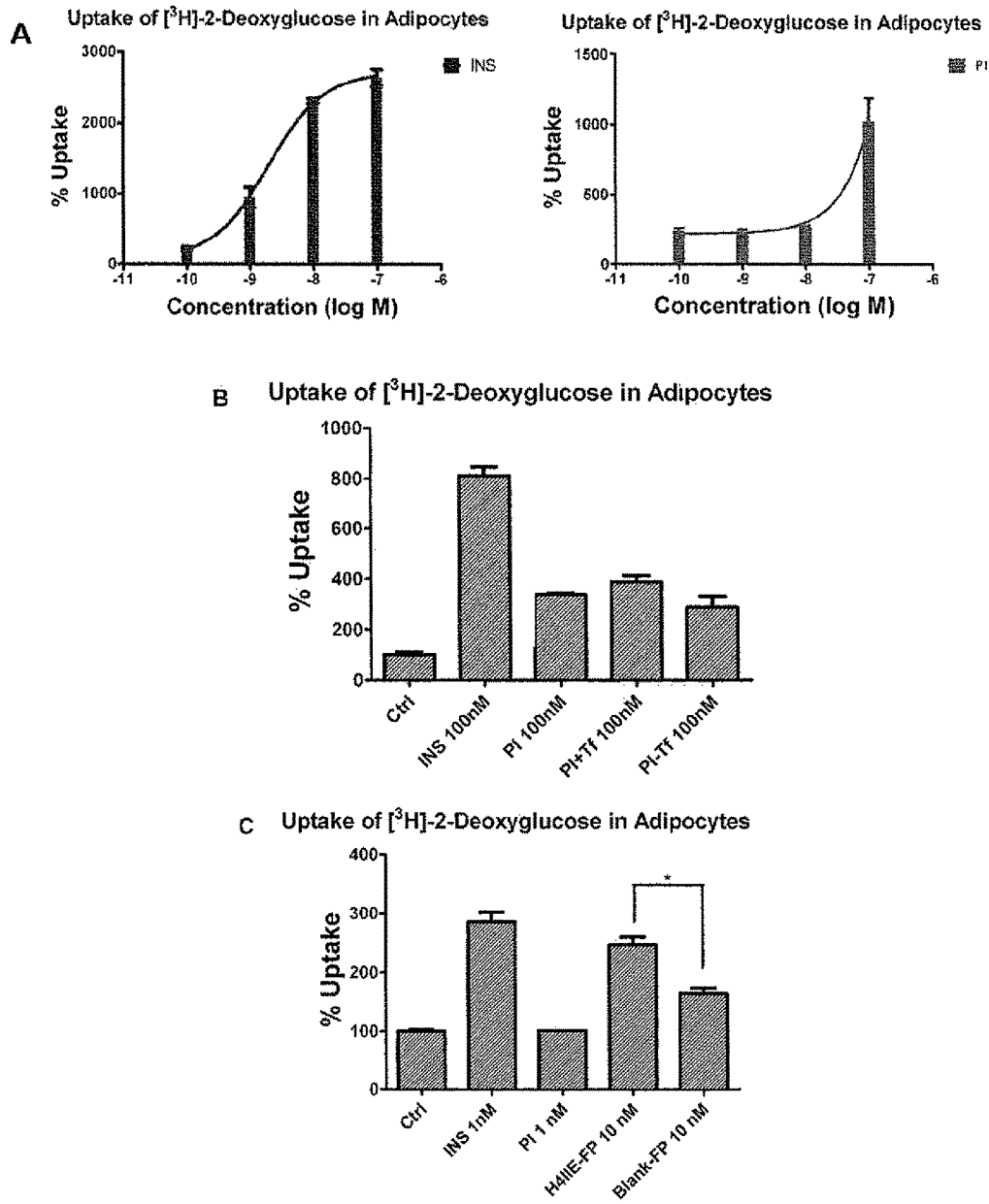
FIG. 6 shows a bar graph of glucose uptake by adipocytes. It demonstrates the uptake of 2-deoxy-D-[2,6-3H] glucose into cultured adipocytes is stimulated by H4IIE-pretreated PI-Tf fusion protein. (A) Dose-dependent curve of glucose uptake stimulation by insulin and proinsulin. (B) Comparison of glucose uptake by 100 nM insulin, proinsulin, proinsulin and Tf in equamolar ratio, and PI-Tf fusion protein. (C) H4IIE-pretreated PI-Tf fusion protein exhibited increased activity, compared with non-cell-treated fusion protein. Asterisk indicated p<0.01 evaluated from t-test.

Insulin exhibited a strong stimulation in glucose uptake with EC50 values of 2 nM, whereas proinsulin was much less active (FIG. 6A). This is due to the much lower binding affinity of proinsulin to insulin receptor. Similar to proinsulin, PI-Tf fusion protein also exerted low stimulatory activity for the 30-min glucose uptake (FIG. 6B). However, when PI-Tf fusion protein pretreated in H4IIE cells was used to treat adipocytes, there showed a significantly increased glucose uptake, compared with PI-Tf pretreated in blank wells under the same experimental conditions (FIG. 6C). This result demonstrated that the insulin-Tf converted by hepatoma cells was biologically active in stimulating glucose uptake. Therefore, hepatic pretreatment can sufficiently convert and activate PI-Tf fusion proteins. These data implied the application of PI-Tf fusion proteins as a prodrug for treatment of diabetes through either invasive or non-invasive delivery routes.

Example 5

Prolonged in vivo Plasma Half-Life of ProINS-Tf Fusion Protein

Figure 7:
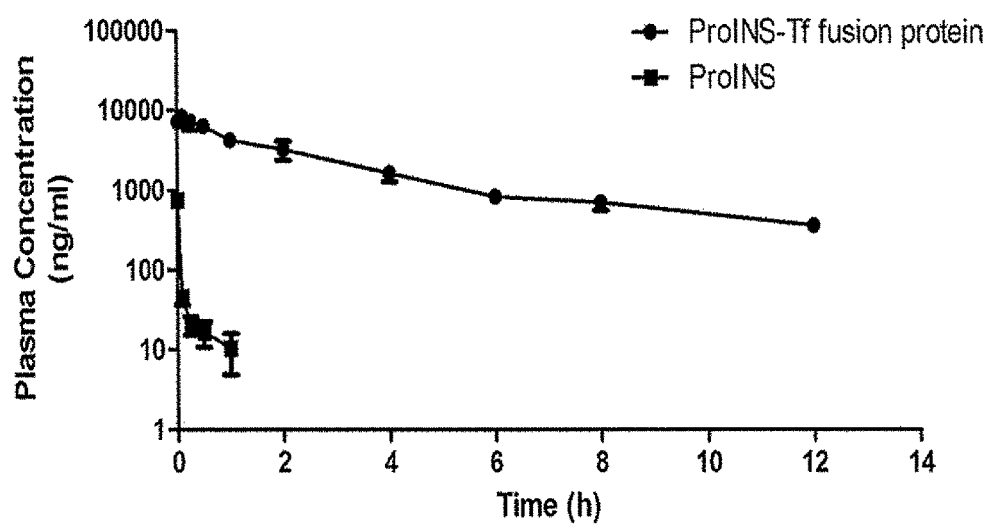
FIG. 7 shows a comparison of in vivo pharmacokinetic profiles of an exemplary ProINS-Tf fusion protein and ProINS.

A single dose of 0.5 mg/kg ProINS-Tf or 0.053 mg/kg ProINS was injected intravenously to CF-1 mice. Plasma concentrations of ProINS-Tf and ProINS were measured by ProINS-specific RIA (Millipore, Mass.). Data were obtained from 4 mice and shown in FIG. 7.

In Vivo Pharmacokinetics.

Male CF-1 mice (6-7 weeks old) were fasted for 6 h prior to drug administration. A single dose of ProINS-Tf or ProINS was injected intravenously. Blood was sampled at different time points through saphenous veins. Whole blood was mixed with heparin and centrifuged to collect plasma. Plasma concentrations of ProINS-Tf and ProINS were determined by ProINS-specific RIA using ProINS-Tf and ProINS as standard curve, respectively.

Example 6

Figure 8:
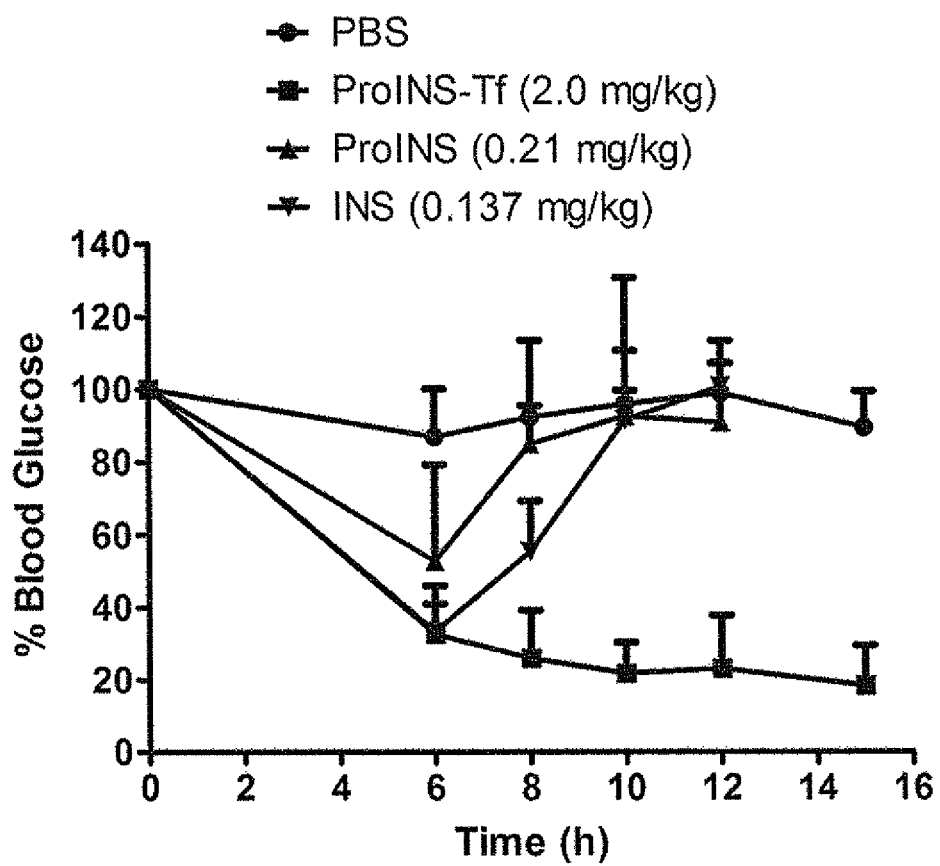
FIG. 8 shows a comparison of the in vivo hypoglycemic efficacy of an exemplary ProINS-Tf fusion protein against PBS, INS, and ProINS.

Sustained and Enhanced In Vivo Hypoglycemic Efficacy of ProINS-Tf Fusion Protein STZ-induced diabetic mice were given a single subcutaneous injection of PBS, INS, ProINS, or ProINS-Tf fusion proteins with the same molar dose. Mice were fasted during experiments. Blood glucose levels were measured using OneTouch glucose meter. All the time points indicate hours post-injection. Data are expressed as the percentage of blood glucose compared to 0 h (initial blood glucose levels prior to injection). FIG. 8 and the following table summarizes the result of the experiment. Data represent averages±standard deviation ($N=3-5$).

| Injection Groups | 6 h | 8 h | 10 h | 12 h |
|---|---|---|---|---|
| PBS | 87.1 ± 13.2 | 92.5 ± 3.25 | 96.2 ± 3.67 | 99.2 ± 8.22 |
| INS (3 U/kg, 0.137 mg/kg) | 33.4 ± 7.58 | 55.5 ± 14.1 | 91.7 ± 39.3 | 109.9 ± 12.8 |
| ProINS (0.21 mg/kg) | 52.7 ± 26.6 | 85.1 ± 28.5 | 92.9 ± 18.1 | 91.2 ± 16.4 |
| ProINS-Tf (2 mg/kg) | 32.6 ± 13.4 | 26.0 ± 13.3 | 21.8 ± 8.44 | 23.1 ± 14.7 |

In Vivo Hypoglycemic Efficacy.

Male C57BL/6J mice (6-7 weeks old) were given a single intraperitoneal injection of 175 mg/kg streptozotocin. Six days post-injection, mice became diabetic with fasting blood glucose levels ~500 mg/dL. Diabetic mice were fasted for 2 h prior to a single subcutaneous injection of proteins. Blood was sampled through tail veins at various time points. Blood glucose levels were measured using OneTouch glucose meter.

Example 7

Prolonged Suppression of Blood Glucose Levels Under Fasting Conditions Following Treatment with Proinsulin-Transferrin (ProINS-Tf)

Figure 9:
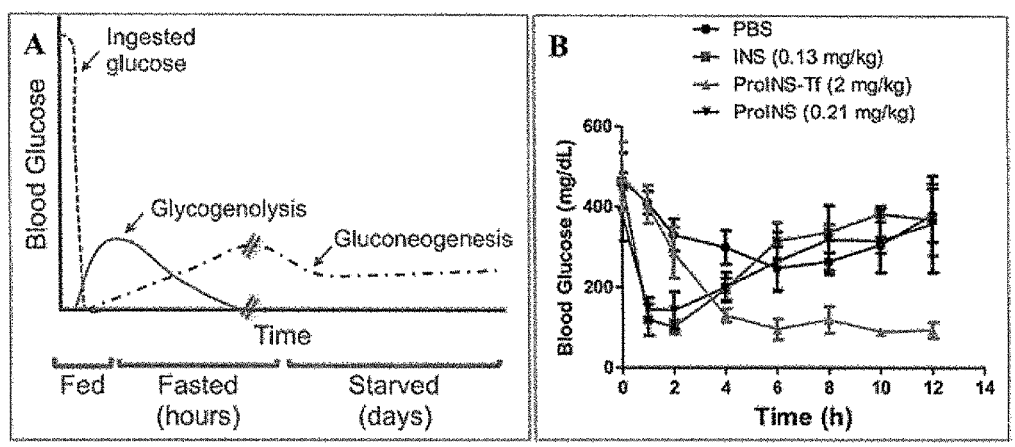
FIG. 9 shows the importance of the hepatic glucose production pathway and prolonged suppression of blood glucose levels. (A) Sources of blood glucose in fed and fasted states. (B) STZ-mice were given a single s.c. injection of PBS, or 22.5 nmol/kg INS, ProINS, or ProINS-Tf. Mice were fasted 2 h prior to injection and during experiments. Blood glucose levels were measured using OneTouch glucose meter. Data represent average±standard deviation (n=3-5).

Hepatic glucose production (HGP), through the glycogenolysis and gluconeogenesis pathways, is a crucial pathway for glucose homeostasis to maintain normal glucose levels in the blood. Under fasting and starved conditions, the primary source of glucose in the blood is through HGP (FIG. 9A). Therefore, in order to evaluate the effect of ProINS-Tf on HGP, the blood glucose levels at long time points post-injection were evaluated. Male C57Bl/6 mice (6-7 weeks old) were treated with a single i.p. injection of 150 mg/kg streptozotocin (STZ), and mice with fasting blood glucose levels ~500 mg/dL were considered diabetic. Mice were given a single s.c. injection of buffer control (PBS), INS, proinsulin (ProINS), or ProINS-Tf, and the blood glucose levels were measured at various timepoints post-administration under fasting conditions. As shown in FIG. 9B, the hypoglycemic effect of ProINS-Tf gradually increased, with a maximum effect at 4 h post-injection that was maintained at normoglycemic levels (i.e. similar to non-STZ induced mice) until the latest 12 h timepoint tested (72-77% decrease compared to PBS). Blood glucose levels of ProINS and INS were not significantly different from the PBS group beginning at 8 and 10 h post administration, respectively. Therefore, the data shown in FIG. 9B demonstrates that ProINS-Tf specifically inhibits HGP, as indicated by the prolonged suppression of blood glucose levels under fasting conditions.

Example 8

Effect of ProINS-Tf on HGP Enzyme Levels

In order to evaluate the effect of ProINS-Tf on HGP, mRNA levels of glucose-6-phosphatase (G6Pase) were determined in ProINS-Tf treated STZ-mice. G6Pase is a key enzyme that catalyzes the terminal step in the HGP pathway. STZ-mice were treated with ProINS-Tf or buffer control for 12 h, and the G6Pase expression level was determined in liver homogenates using RT-PCR. The results showed that the expression of G6Pase in ProINS-Tf-treated mice was only ~10% of the control mice, indicating the inhibition of HGP.

REFERENCES

The following cited references are each incorporated herein by reference.

[1] Rholam M and Fahy C. Processing of Peptide and Hormone Precursors at the Dibasic Cleavage Sites. *Cell. Mol. Life Sci.* 2009, 66, 2075-2091.

[2] Smeekens S. P. Processing of Protein Precursors by a Novel Family of Subtilisin-Related Mammalian endoproteases. *Nat. Biotech.*, 1993, 11, 182-186.

[3] Wurm F. M. Production of Recombinant Protein Therapeutics in Cultivated Mammalian Cells. *Nat. Biotech.*, 2004, 22, 1393-1398.

[4] Wong, D. W. S. Microbial Production of Recombinant Human Insulin. *The ABCs of Gene Cloning* (2$^{nd}$ Ed), 2007, Springer US, pp. 159-162.

[5] Raemy-Schenk A-M., Trouble S., Gaillard P. et al. A Cellular Assay for Measuring the Modulation of Glucose Production in H4IIE Cells. *Assay Drug Dev. Tech.* 2006, 4(5), 525-533.

[6] Levy, J. R., Ullrich, A., Olefsky, J. M. Endocytotic Uptake, Processing, and Retroendocytosis of Human Biosynthetic Proinsulin by Rat Fibroblasts Transfected with the Human Insulin Receptor Gene. J. Clin. Invest, 1988, 81, 1370-1377.

[7] Johansson G. S. and Arnqvist H. J. Insulin and IGF-1 Action on Insulin Receptors, IGF-1 Receptors, and Hybrid Insulin/IGF-1 Receptors in Vascular Smooth Muscle Cells. *Am. J. Physiol. Endocrinol. Metab.* 2006, 291, E1124-E1130.

[8] Harmon A. W., Paul D. S., Patel Y. M. MEK Inhibitors Impair Insulin-Stimulated Glucose Uptake in 3T3-L1 Adipocytes. *Am. J. Physiol. Endocrinol. Metab.* 2004, 287, E758-E766.

[9] Pickup J C, Renard E. Long-Acting Insulin Analogs Versus Insulin Pump Therapy for the Treatment of Type 1 and Type 2 Diabetes. *Diabetes Care.* 2008; 31:S140-S5.

[10] Saltiel A R, Pessin J E. Mechanism of Insulin Action (*Medical Intelligence Unit*). New York: Springer; 2007.

[11] Vienberg S G, Bouman S D, Sorensen H, Stidsen C E, Kjeldsen T, Glendorf T, et al. Receptor-isoform-selective insulin analogues give tissue-preferential effects. *Biochemical Journal.* 2011; 440(3):301-8.

[12] Agouni A, Owen C, Czopek A, Mody N, Delibegovic M. In vivo differential effects of fasting, re-feeding, insulin and insulin stimulation time course on insulin signaling pathway components in peripheral tissues. *Biochemical and Biophysical Research Communications*. 2010; 401(1):104-11.

What is claimed is:

1. A method of delivering a proinsulin protein to the liver of a subject, comprising:
   administering by injection a proinsulin transferrin fusion protein to a subject in need thereof,
   wherein said proinsulin transferrin fusion protein comprises a preproinsulin sequence linked to a transferrin (Tf) sequence via a linker sequence, wherein the linker sequence consists of a leucine-glutamate dipeptide linker sequence, and
   wherein the proinsulin transferrin protein is delivered to the liver in an amount effective to produce a normoglycemic level relative to a phosphate buffered saline (PBS) control at 12 hours post-injection under fasting conditions.

2. The method of claim 1, wherein the effective amount of proinsulin transferrin fusion protein is an amount sufficient to reduce hepatic glucose production.

3. The method of claim 1, wherein proinsulin transferrin fusion protein is administered in a single injection.

4. The method of claim 1, wherein the proinsulin transferrin protein is delivered to the liver in an amount effective to reduce mRNA levels of glucose-6-phosphatase.

5. A method for reducing hepatic glucose production in a subject in need thereof, comprising:
   administering by injection to said subject an effective amount of a proinsulin transferrin fusion protein,
   wherein said proinsulin transferrin fusion protein comprises a preproinsulin sequence linked to a transferrin (Tf) sequence via a linker sequence, wherein the linker sequence consists of a leucine-glutamate dipeptide linker sequence, and
   wherein the effective amount is sufficient to produce a normoglycemic level relative to a phosphate buffered saline (PBS) control at 12 hours post-injection under fasting conditions.

6. The method of claim 5, wherein the effective amount is injected in a single injection.

7. The method of claim 5, wherein the effective amount is an amount sufficient to reduce mRNA levels of glucose-6-phosphatase.

8. The method of claim 1 or claim 5, wherein the injection is intravenous or subcutaneous.

* * * * *

SEQUENCE LISTING

<160> NUMBER OF SEQ ID NOS: 2

<210> SEQ ID NO 1
<211> LENGTH: 469
<212> TYPE: DNA
<213> ORGANISM: Homo sapiens

<400> SEQUENCE: 1

```
agccctccag gacaggctgc atcagaagag gccatcaagc agatcactgt ccttctgcca        60
tggccctgtg gatgcgcctc ctgccctgc tggcgctgct ggccctctgg ggacctgacc        120
cagccgcagc ctttgtgaac caacacctgt gcggctcaca cctggtggaa gctctctacc        180
tagtgtgcgg ggaacgaggc ttcttctaca cacccaagac ccgccgggag gcagaggacc        240
tgcaggtggg gcaggtggag ctgggcgggg gccctggtgc aggcagcctg cagcccttgg        300
ccctggaggg gtccctgcag aagcgtggca ttgtggaaca atgctgtacc agcatctgct        360
ccctctacca gctggagaac tactgcaact agacgcagcc cgcaggcagc cccacacccg        420
ccgcctcctg caccgagaga gatggaataa agcccttgaa ccagcaaaa                    469
```

<210> SEQ ID NO 2
<211> LENGTH: 2808
<212> TYPE: DNA
<213> ORGANISM: Homo sapiens

<400> SEQUENCE: 2

```
tggcaccgag cgagccgcga tgacaatggc tgcattgtgc ttcatgtccc ttcccatcaa        60
catttctgtg ctggactcct ccactcgcg ggtcgtctcc agagctcaga aaatgaggtg        120
atcagtggga cgagtaagga agggggttg ggagaggggc gattgggcaa cccggctgca        180
caaacacggg aggtcaaaga ttgcgcccag cccgcccagg ccgggaatgg aataaaggga        240
cgcggggcgc cggaggctgc acagaagcga gtccgactgt gctcgctgct cagcgccgca        300
cccggaagat gaggctcgcc gtgggagccc tgctggtctg cgccgtcctg gggctgtgtc        360
tggctgtccc tgataaaact gtgagatggt gtgcagtgtc ggagcatgag gccactaagt        420
gccagagttt ccgcgaccat atgaaaagcg tcattccatc cgatggtccc agtgttgctt        480
gtgtgaagaa agcctcctac cttgattgca tcagggccat tgcggcaaac gaagcggatg        540
ctgtgacact ggatgcaggt ttggtgtatg atgcttacct ggctcccaat aacctgaagc        600
ctgtggtggc agagttctat gggtcaaaag aggatccaca gactttctat tatgctgttg        660
ctgtggtgaa gaaggatagt ggcttccaga tgaaccagct tcgaggcaag aagtcctgcc        720
acacgggtct aggcaggtcc gctgggtgga acatccccat aggcttactt tactgtgact        780
tacctgagcc acgtaaacct cttgagaaag cagtggccaa tttcttctcg gcagctgtg        840
cccttgtgc ggatgggacg gacttccccc agctgtgtca actgtgtcca gggtgtggct        900
gctccaccct taaccaatac ttcggctact cgggagcctt caagtgtctg aaggatggtg        960
ctggggatgt ggcctttgtc aagcactcga ctatatttga gaacttggca acaaggctg       1020
acaggaccac gtatgagctg ctttgcctgg acaacacccg gaagccggta gatgaataca       1080
aggactgcca cttggcccag gtcccttctc ataccgtcgt ggcccgaagt atgggcggca       1140
aggaggactt gatctgggag cttctcaacc aggcccagga acattttgc aaagacaaat       1200
caaaagaatt ccaactattc agctctcctc atgggaagga cctgctgttt aaggactctg       1260
cccacgggtt tttaaaagtc cccccagga tggatgccaa gatgtacctg ggctatgagt       1320
atgtcactgc catccggggaat ctacgggaag gcacatgccc agaagcccca acagatgaat       1380
gcaagcctgt gaagtggtgt gcgctgagcc accacgagag gctcaagtgt gatgagtgga       1440
gtgttaacag tgtagggaaa atagagtgtg tatcagcaga gaccaccgaa gactgcatcg       1500
ccaagatcat gaatggagaa gctgatgcca tgagcttgga tggagggttt gtctacatag       1560
```

```
cgggcaagtg tggtctggtg cctgtcttgg cagaaaacta caataagagc gataattgtg    1620
aggatacacc agaggcaggg tattttgctg tagcagtggt gaagaaatca gcttctgacc    1680
tcacctggga caatctgaaa ggcaagaagt cctgccatac ggcagttggc agaaccgctg    1740
gctggaacat ccccatgggc ctgctctaca ataagatcaa ccactgcaga tttgatgaat    1800
ttttcagtga aggttgtgcc cctgggtcta agaaagactc cagtctctgt aagctgtgta    1860
tgggctcagg cctaaacctg tgtgaaccca acaacaaaga gggatactac ggctacacag    1920
gcgctttcag gtgtctggtt gagaagggag atgtggcctt tgtgaaacac cagactgtcc    1980
cacagaacac tggggaaaa aaccctgatc catgggctaa gaatctgaat gaaaaagact     2040
atgagttgct gtgccttgat ggtaccagga aacctgtgga ggagtatgcg aactgccacc    2100
tggccagagc cccgaatcac gctgtggtca cacggaaaga taaggaagct tgcgtccaca    2160
agatattacg tcaacagcag cacctatttg gaagcaacgt aactgactgc tcgggcaact    2220
tttgtttgtt ccggtcggaa accaaggacc ttctgttcag agatgacaca gtatgtttgg    2280
ccaaacttca tgacagaaac acatatgaaa atacttagg agaagaatat gtcaaggctg     2340
ttggtaacct gagaaaatgc tccacctcat cactcctgga agcctgcact ttccgtagac    2400
cttaaaatct cagaggtagg gctgccacca aggtgaagat gggaacgcag atgatccatg    2460
agtttgccct ggtttcactg gcccaagtgg tttgtgctaa ccacgtctgt cttcacagct    2520
ctgtgttgcc atgtgtgctg aacaaaaaat aaaaattatt attgatttta tatttcaaaa    2580
actccattct ttcctaaata ttttcaacaa aggatttctt tatgcattct gcctaaatac    2640
ctatgcaact gagcccttcc ttctcagctc aagattcgtc tggtctttcc ctacagcttt    2700
gtgtgtgcca tggccacatc tcctgggtac agttcaagga gacatctttt ctaaagggt    2760
ctgcgtgatc attaaaatat aatcaaatgt aaaaaaaaaa aaaaaaaa               2808
```